(12) United States Patent
Schubert et al.

(10) Patent No.: US 9,315,614 B2
(45) Date of Patent: Apr. 19, 2016

(54) URETHANE-CONTAINING SILYLATED PREPOLYMERS AND PROCESS FOR PREPARATION THEREOF

(75) Inventors: Frank Schubert, Neukirchen-Vluyn (DE); Michael Ferenz, Essen (DE); Wilfried Knott, Essen (DE)

(73) Assignee: Evonik DeGussa GmbH, Essen (DE)

( * ) Notice: Subject to any disclaimer, the term of this patent is extended or adjusted under 35 U.S.C. 154(b) by 651 days.

(21) Appl. No.: 12/859,731

(22) Filed: Aug. 19, 2010

(65) Prior Publication Data
US 2011/0046305 A1 Feb. 24, 2011

(30) Foreign Application Priority Data
Aug. 19, 2009 (DE) .................. 10 2009 028 636

(51) Int. Cl.
| | | |
|---|---|---|
| C08G 18/50 | (2006.01) | |
| C08G 18/38 | (2006.01) | |
| C08G 18/71 | (2006.01) | |
| C07F 7/10 | (2006.01) | |
| C07F 7/18 | (2006.01) | |
| C07F 7/02 | (2006.01) | |
| C07F 7/08 | (2006.01) | |
| C08G 18/12 | (2006.01) | |
| C08G 18/20 | (2006.01) | |
| C08G 18/22 | (2006.01) | |
| C08G 18/28 | (2006.01) | |
| C08G 18/48 | (2006.01) | |
| C08G 18/75 | (2006.01) | |
| C08G 18/79 | (2006.01) | |

(52) U.S. Cl.
CPC ............ *C08G 18/5096* (2013.01); *C07F 7/025* (2013.01); *C07F 7/081* (2013.01); *C07F 7/0812* (2013.01); *C07F 7/0818* (2013.01); *C07F 7/10* (2013.01); *C07F 7/18* (2013.01); *C07F 7/1804* (2013.01); *C08G 18/12* (2013.01); *C08G 18/2063* (2013.01); *C08G 18/227* (2013.01); *C08G 18/289* (2013.01); *C08G 18/3893* (2013.01); *C08G 18/4854* (2013.01); *C08G 18/71* (2013.01); *C08G 18/718* (2013.01); *C08G 18/755* (2013.01); *C08G 18/792* (2013.01)

(58) Field of Classification Search
USPC .................. 528/28, 48, 49, 76, 79, 80, 84, 85
IPC ........ C08G 18/2835, 18/289, 18/3203, 18/3893,
C08G 18/4009, 18/4081, 18/5096, 18/61,
C08G 18/615, 18/6469, 18/0838, 18/10, 18/12,
C08G 18/282, 18/2825, 18/283, 18/792, 18/71;
C07F 7/025, 7/081, 7/0812, 7/0818, 7/18,
C07F 7/1804, 7/10

See application file for complete search history.

(56) References Cited

U.S. PATENT DOCUMENTS

| | | | |
|---|---|---|---|
| 5,430,166 A | 7/1995 | Klein et al. | |
| 5,475,127 A | 12/1995 | Klein et al. | |
| 6,291,622 B1 | 9/2001 | Droese et al. | |
| 6,307,082 B1 | 10/2001 | Klein et al. | |
| 6,585,663 B1 | 7/2003 | Coley et al. | |
| 7,125,585 B2 | 10/2006 | Dudzik et al. | |
| 7,157,541 B2 | 1/2007 | Knott et al. | |
| 7,196,153 B2 | 3/2007 | Burkhart et al. | |
| 7,598,334 B2 | 10/2009 | Ferenz et al. | |
| 7,612,158 B2 | 11/2009 | Burkhart et al. | |
| 7,612,159 B2 | 11/2009 | Burkhart et al. | |
| 7,619,035 B2 | 11/2009 | Henning et al. | |
| 7,635,581 B2 | 12/2009 | Ferenz et al. | |
| 7,645,848 B2 | 1/2010 | Knott et al. | |
| 7,727,599 B2 | 6/2010 | Dohler et al. | |
| 8,268,939 B2 * | 9/2012 | Ebbrecht et al. | ............. 525/476 |
| 2006/0188455 A1 | 8/2006 | Ferenz et al. | |
| 2006/0188456 A1 | 8/2006 | Ferenz et al. | |
| 2007/0128143 A1 | 6/2007 | Gruening et al. | |
| 2007/0287765 A1 | 12/2007 | Busch et al. | |
| 2008/0027202 A1 | 1/2008 | Ferenz et al. | |
| 2008/0076842 A1 | 3/2008 | Ferenz et al. | |
| 2008/0153934 A1 | 6/2008 | Neumann et al. | |
| 2008/0153992 A1 | 6/2008 | Knott et al. | |
| 2008/0153995 A1 | 6/2008 | Knott et al. | |
| 2008/0187702 A1 | 8/2008 | Ferenz et al. | |
| 2008/0305065 A1 | 12/2008 | Ferenz et al. | |
| 2009/0018480 A1 * | 1/2009 | Mager et al. | .................... 602/46 |
| 2009/0030097 A1 | 1/2009 | Knott et al. | |
| 2009/0062459 A1 | 3/2009 | Thum et al. | |
| 2009/0137751 A1 | 5/2009 | Knott et al. | |
| 2009/0137752 A1 | 5/2009 | Knott et al. | |
| 2010/0022435 A1 | 1/2010 | Henning et al. | |
| 2010/0031852 A1 | 2/2010 | Herrwerth et al. | |
| 2010/0034765 A1 | 2/2010 | Herrwerth et al. | |
| 2010/0036011 A1 | 2/2010 | De Gans et al. | |
| 2010/0041910 A1 | 2/2010 | Schubert et al. | |
| 2010/0056649 A1 | 3/2010 | Henning et al. | |
| 2010/0056818 A1 | 3/2010 | Ferenz et al. | |
| 2010/0071849 A1 | 3/2010 | Knott et al. | |
| 2010/0081763 A1 | 4/2010 | Meyer et al. | |
| 2010/0081781 A1 | 4/2010 | Schubert et al. | |

(Continued)

FOREIGN PATENT DOCUMENTS

| | | |
|---|---|---|
| GB | 1 113 228 A | 5/1968 |
| WO | WO 01/21718 A1 | 3/2001 |

(Continued)

*Primary Examiner* — Rabon Sergent
(74) *Attorney, Agent, or Firm* — Frommer Lawrence & Haug LLP

(57) ABSTRACT

Novel urethane- and silyl-containing prepolymers and compositions obtained as reaction products from alkoxysilyl-bearing compounds and isocyanate-bearing compounds, and a process for preparation thereof.

14 Claims, 1 Drawing Sheet

(56) References Cited

U.S. PATENT DOCUMENTS

2010/0105843 A1    4/2010    Knott et al.
2010/0113633 A1    5/2010    Henning et al.
2010/0184913 A1*   7/2010    Ebbrecht et al. ............. 524/588

FOREIGN PATENT DOCUMENTS

| | | |
|---|---|---|
| WO | WO 2005/078036 A1 | 8/2005 |
| WO | WO 2009/065644 | 5/2009 |
| WO | WO 2009/100793 | 8/2009 |

\* cited by examiner

Silyl polyether 1 of the formula (1)
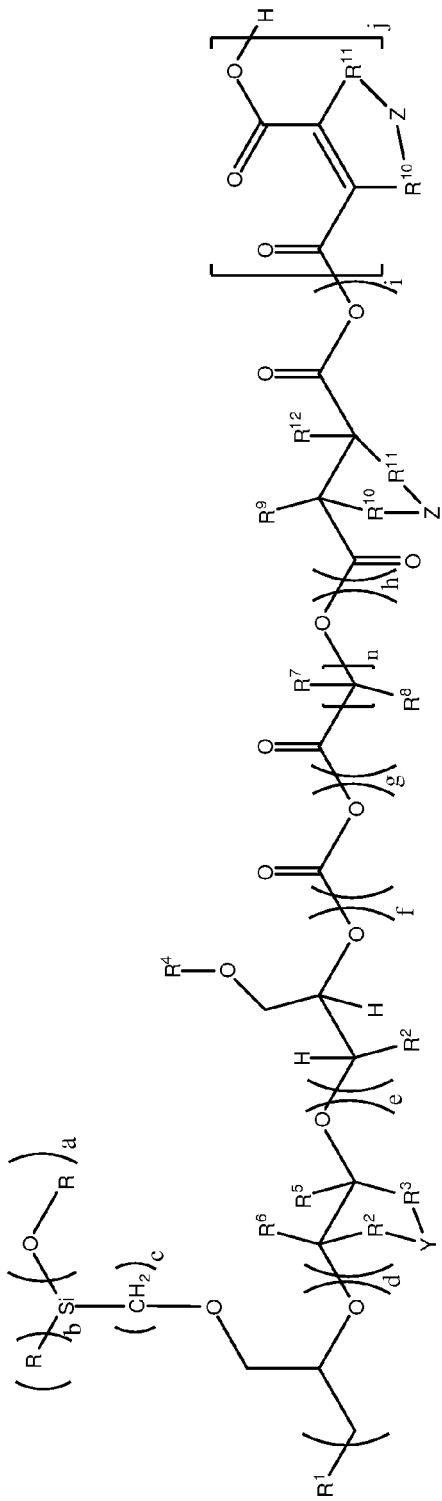

URETHANE-CONTAINING SILYLATED PREPOLYMERS AND PROCESS FOR PREPARATION THEREOF

This application claims benefit under 35 U.S.C. 119(a) of German patent application DE 10 2009 028636.5, filed on Aug. 19, 2009.

Any foregoing applications including German patent application DE 10 2009 028636.5, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to novel urethane-containing reaction products formed from silyl polyethers and isocyanate-bearing compounds, and to a process for preparing such reaction products.

Polymers and oligomers which are prepared from isocyanate-bearing compounds by reaction with hydroxyl- or amine-functional compounds have been known for some time and in a wide chemical variety. According to the stoichiometry of the reaction and type of starting compounds, prepolymers having urethane or urea groups are thus formed, which bear terminally reactive isocyanate, hydroxyl or amine groups and, in the synthesis, can either be converted further in a subsequent step or else frequently can be used as crosslinkable base materials for adhesives and sealants, or else as coating materials. Particularly widespread and of economic significance are isocyanate-bearing urethane prepolymers. For instance, U.S. Pat. No. 4,038,304 describes the preparation of a prepolymer by reacting 1 mol of trimethylolpropane with 3 mol of isophorone diisocyanate (IPDI) to give an isocyanate-functional prepolymer.

Likewise known are isocyanate-terminated urethane prepolymers which are formed by the reaction of a polyetherpolyol with molar excesses of an organic diisocyanate monomer and in which the excess of the diisocyanate monomer is optionally removed by distillation. For example, the teachings of the documents UK Patent No. 1,101,410 and U.S. Pat. Nos. 5,703,193, 4,061,662, 4,182,825, 4,385,171, 4,888,442 and 4,278,577 are directed to such prepolymers. Specifically in the case of the polyurethane elastomers, the prepolymers derive frequently from toluene diisocyanate and a series of polyols which may include polyethers, polyesters and polycaprolactones, and similar compound classes. Ultimately, the selection of the reactive components by type and amount used is determined by the desired profile of properties of the polyurethane with regard to physical, chemical and dynamic properties. For instance, the isocyanate content of the prepolymer determines the Shore A hardness.

EP-A1-0 511 566 (U.S. Pat. No. 5,166,302) describes moisture-curing NCO-reactive polyurethane hotmelt adhesives which are obtained by an addition reaction of polyols with polyisocyanates. The reaction products in such reactions of polyfunctional starting compounds are frequently, in terms of the chemical composition and molar mass thereof, complex mixtures of prepolymers. Addition of isocyanate compounds onto urethane groups which have already formed can also form allophanate structures to different degrees according to the reaction regime. Generally, it is difficult to prevent polymerizations on isocyanate groups with one another from taking place, and also branched prepolymer structures from forming. The prior art therefore includes numerous process variants in the synthesis of prepolymers from isocyanates and OH- or amine-functional compounds, with the aim, through skilful selection of catalysts, reaction conditions and monomeric starting compounds, of obtaining defined chemical structures and products with usually very low viscosity and low molar mass distribution.

DE 10 2006 056478 discloses one variant of the prepolymer synthesis, in which the further reaction to give high molecular weight prepolymer structures is counteracted by the use of polyisocyanates with NCO groups of different reactivity. WO 99/24486 (U.S. Pat. No. 6,784,242) discloses a two-stage process for preparing a polyurethane binder with a particularly low content of monomeric, unconverted isocyanate compounds.

Additionally known are urethane prepolymers which contain curable functional groups such as silane groups.

Alkoxysilane-functional polyurethanes which crosslink via a silane condensation have been known for a long time. A review article on this subject can be found, for example, in "Adhesives Age" April 1995, pages 30 ff. (authors: Ta-Ming Feng, B. A. Waldmann). Such alkoxysilane-terminated, moisture-curing one-component polyurethanes are being used to an increasing degree as flexible coating, sealing and adhesive materials in construction and in the automotive industry.

Such alkoxysilane-functional polyurethanes can be prepared according to U.S. Pat. No. 3,627,722 or U.S. Pat. No. 3,632,557 by, for example, reacting polyetherpolyols with an excess of polyisocyanate to give an NCO-containing prepolymer, which is then in turn reacted further with an amino-functional alkoxysilane. The alkoxysilane-functional prepolymer which forms contains urea and urethane groups in high concentration, which lead to a high viscosity of the products.

An effective concept for reducing at least the proportion of the hydrogen bond density caused by the urea groups is to use secondary aminosilanes to obtain substituted ureas. For this purpose, various processes have been proposed: U.S. Pat. No. 3,627,722 and U.S. Pat. No. 3,632,557 use alkyl-substituted aminosilanes, U.S. Pat. No. 4,067,844 adds acrylates onto the primary aminosilane, and EP-A1 676 403 introduces aryl-substituted aminosilanes. All these processes, however, can replace only one hydrogen atom on the terminal urea group; all further urea and urethane protons still contribute to a high viscosity via hydrogen bonds.

DE 10 2005 041954 A1 (US 2007-0055010) describes urethane prepolymers which have alkoxysilyl groups and are allophanate-modified, the allophanate structure of which has a moisture-curing silane-functional radical.

Silane-functional urethane prepolymers, also referred to as silane-terminated polyurethanes, no longer contain any free NCO groups according to the prior art. Reaction with, for example, alkoxysilanes bearing amino groups forms urea groups as a link between the prepolymer and the actually desired curable terminal alkoxysilyl groups.

Tied to this idea of curable terminal alkoxysilyl groups, Momentive describes, in U.S. Pat. No. 7,524,915, moisture-curable polymers which are obtained by the reaction of one or more polyetherpolyols with one or more polyisocyanates and one or more isocyanate-functional silanes. These compounds are characterized in that the silyl groups are present only at the chain ends of the polymer backbone.

Dow Chemical describes, in U.S. Pat. No. 6,162,862, polyfunctional liquid urethane-containing adducts which, as well as an isocyanate function, may also contain a silyl function.

These products are obtained by the reaction of an isocyanate-containing intermediate with a polyfunctional substance. Among other ways, the isocyanate-containing intermediates can be prepared by the reaction of polyethers with polyfunctional isocyanates. Remaining isocyanate functions are then reacted with substances which possess two or more isocyanate-reactive groups. In this manner, for example, it is said to be possible also to introduce silyl groups into the product. The products obtained are suitable, for example, for the coating of surfaces, for example as a constituent in paints. When silyl-containing polymers are prepared by these processes, the silyl groups can be attached only via the isocyanate functions.

The known processes therefore lack the freedom, beyond the known α,ω-functionalization principle, to make obtainable prepolymer structures which possess a molecular presence of curable moieties (=sum of isocyanato and silyl functions per molecule) greater than 2 and additionally give a means of selection entirely at the discretion of the synthetic chemist to adjust the ratio of the curable moieties (isocyanato/alkoxysilyl functions) relative to one another within wide ranges according to the performance requirements which are the aim thereof.

Furthermore, it is a deficiency known to those skilled in the art that conventional silyl-terminated polyurethanes are employable only to a restricted degree owing to the high viscosity caused by their chemical structure, as emphasized in U.S. Pat. No. 7,365,145. This is particularly true when, in the sealant and adhesive systems sector, customary amounts of 30-50% by weight of inorganic fillers such as calcium carbonate or silicates are added. Diluents are therefore added to polymers of this type according to the prior art. These may either be reactive diluents, which do not only lower the viscosity but simultaneously increase the crosslinking density, such as monomeric alkoxysilanes, or else nonreactive diluents or solvents which may additionally have plasticizing properties. A typical representative of this class of silyl-terminated polyurethanes is, for example, Desmoseal© S XP 2636 from Bayer Material Science with a viscosity of approx. 40 000 mPas (23° C.).

With the aid of controlled allophanatization, attempts are made in the prior art to counteract the high viscosities based on strong intermolecular hydrogen bonds and dipolar interactions of the urethane and any urea units with one another, but without being able to eliminate the shortcoming of low crosslinking density.

WO 2007/025667 (US 2007-0055010) describes polyurethane prepolymers having modified alkoxysilane groups, which are said to have a significantly reduced viscosity. However, a disadvantage is the relatively low density of crosslinkable silane groups.

Acknowledging the prior art described here, the technical problem to be solved is defined as providing novel urethane-containing silylated prepolymers which avoid the described disadvantages of known alkoxysilane-modified polyurethane prepolymers.

The object is achieved by novel reaction products formed from alkoxysilyl compounds and isocyanates, which may bear one, two or else more than two isocyanate groups. The alkoxysilyl compound preferably bears at least 1 free hydroxyl group.

The present invention thus provides urethane-containing (pre)polymers and/or reaction products, obtainable by the reaction of
a) at least one compound having one or more isocyanate groups with
b) at least one compound bearing one or more alkoxysilyl groups and additionally bearing at least one hydroxyl group,
c) optionally in the presence of one or more catalysts,
d) optionally in the presence of further components reactive towards the reaction products, especially those which possess functional groups with protic hydrogen, for example alcohols, amines, thiols, organofluorine hydroxyl compounds, alkoxysilanes and/or water,
e) optionally in the presence of further compounds not reactive towards the reaction products and reactants, for example solvents, processing aids and/or suspension media, and also compositions which comprises these reaction products.

In a preferred embodiment, the component (a) having isocyanate groups bears no alkoxysilyl and/or alkylsilyl groups.

Preferred novel alkoxysilyl-modified urethane-containing reaction products are notable in that they, based on the individual molecule of the reaction product, have an average of more than one alkoxysilyl group per urethane group or reaction conversion products thereof, for example allophanates and/or biuret groups, or else urea groups.

Preference is given to using, as component b) compounds, silyl polyethers of the formula 1 with index d greater than or equal to 1, which additionally have at least one hydroxyl function.

The inventive reaction products are novel alkoxysilyl-modified and urethane-containing compounds, and can be considered as prepolymers. These prepolymers are notable in that the relatively high alkoxysilane functionality and hence crosslinking density thereof can be adjusted in a controlled manner and within wide limits, thus making it possible to avoid, with additionally comparatively lower viscosities, the disadvantages of alkoxysilane-modified polyurethane prepolymers which have been described.

The novel reaction products may, as desired, be modified further either via the isocyanate groups and/or hydroxyl groups present therein, or else via the alkoxysilyl groups incorporated therein.

Indeed, it is thus possible to obtain prepolymers which possess an excess of hydroxyl functions and/or isocyanate functions, in addition to alkoxysilyl groups already present in the starting molecule.

The invention further provides a technically simple and economically viable process for preparing these novel reaction products.

In the process for preparing reaction products, one or more alkoxysilyl-bearing compounds are reacted with isocyanates. In a preferred embodiment of the process, a silyl polyether of the formula 1 is reacted with isocyanates.

This reaction can be performed continuously or batchwise in the presence or absence of a solvent and in the presence of a catalyst.

Completely surprisingly to the person skilled in the art, both the novel prepolymers and a simple technical route for preparation thereof have now been found.

A silyl group in the context of this invention is defined in that it has, as well as at least one alkoxy function, one or two alkyl functions or one or two further alkoxy functions on a silicon atom, where the organic or oxyorganic groups present in the radicals may be the same or different.

Accordingly, the invention also includes the reaction products in which a silyl polyether 1 of the formula (1) can be used as component (b).

The preparation of the silyl polyethers 1 and the usable epoxide structure types are described in detail in DE 10 2008 000360.3 (U.S. Ser. No. 12/389,667), and can thus be prepared, for example, by alkoxylation of epoxy-functional (alkoxy)silanes over double metal cyanide catalysts. The content of the description and of the claims of DE 10 2008 000360.3 (U.S. Ser. No. 12/389,667) is hereby fully incorporated into this disclosure.

The invention therefore also provides a surface modifier (i.e. with respect to texture and finishing, hydrophobicity, stickiness and/or adhesive behaviour) in which component (b) used is a silyl polyether 1 of the formula (1)

methylene units; when Y is absent, $R^2$ and $R^3$ are independently a linear or branched radical having 1 to 20, preferably 1 to 10, carbon atoms, more preferably a methyl, ethyl, propyl or butyl, vinyl, allyl radical or phenyl radical. Preferably, at least one of the two $R^2$ and $R^3$ radicals is hydrogen. $R^2$-$R^3$ may be a —$CH_2CH_2CH_2CH_2$— group, and Y may thus be a —($CH_2CH_2$—)— group. The hydrocarbon radicals $R^2$ and

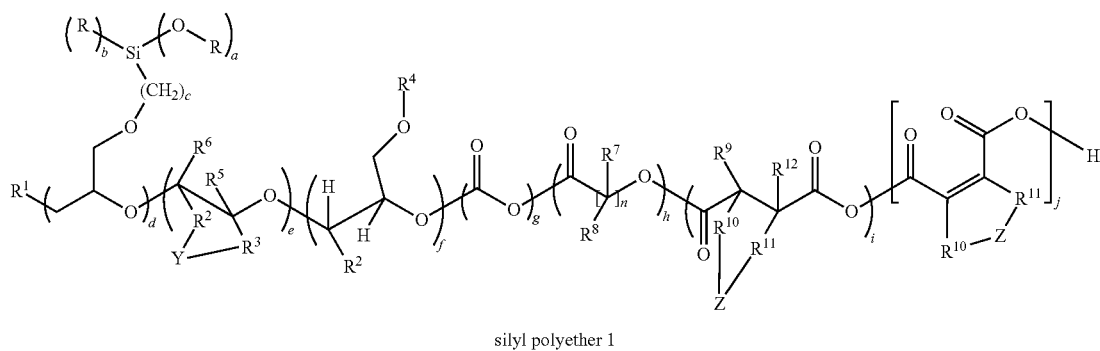

silyl polyether 1 wherein a is an integer from 1 to 3, preferably 3, b is an integer from 0 to 2, preferably 0 to 1, more preferably 0, and the sum of a and b is 3, c is an integer from 0 to 22, preferably from 0 to 12, more preferably from 0 to 8, even more preferably from 0 to 4 and especially 1 or 3, d is an integer from 1 to 500, preferably 1 to 100, more preferably 2 to 20 and especially preferably 2 to 10, e is an integer from 0 to 10 000, preferably 1 to 2000, more preferably 2 to 2000 and especially 2 to 500, f is an integer from 0 to 1000, preferably 0 to 100, more preferably 0 to 50 and especially 0 to 30, g is an integer from 0 to 1000, preferably 0 to 200, more preferably 0 to 100 and especially 0 to 70, h, i and j are each independently integers from 0 to 500, preferably 0 to 300, more preferably 0 to 200 and especially 0 to 100, n is an integer from 2 to 8, R is one or more identical or different radicals selected from linear or branched, saturated, mono- or polyunsaturated alkyl radicals having 1 to 20, especially 1 to 6, carbon atoms or haloalkyl groups having 1 to 20 carbon atoms. R is preferably methyl, ethyl, propyl, isopropyl, n-butyl and sec-butyl groups; and $R^1$ is a hydroxyl group or a saturated or unsaturated, linear, branched or cyclic or further-substituted oxyorganic radical having 1 to 1500 carbon atoms, where the chain may also be interrupted by heteroatoms such as O, S, Si and/or N, or a radical comprising an oxyaromatic system, or preferably an alkoxy, arylalkoxy or alkylarylalkoxy group and especially a polyether radical in which the carbon chain may be interrupted by oxygen atoms, or a singly or multiply fused oxyaromatic group or an optionally branched silicone-containing organic radical, $R^2$ and $R^3$, and $R^5$ and $R^6$, are the same or else independently H or a saturated or optionally mono- or polyunsaturated, also further-substituted, optionally mono- or polyvalent hydrocarbon radical, where the $R^5$ and $R^6$ radicals are each a monovalent hydrocarbon radical. The hydrocarbon radical may be bridged cycloaliphatically via the Y fragment; Y may be absent, or else may be a methylene bridge having 1 or 2

$R^3$ may in turn be further-substituted and bear functional groups such as halogens, hydroxyl groups or glycidyloxypropyl groups, $R^4$ is a linear or branched alkyl radical of 1 to 24 carbon atoms or an aromatic or cycloaliphatic radical which may optionally in turn bear alkyl groups;

$R^7$ and $R^8$ are each independently hydrogen, alkyl, alkoxy, aryl or aralkyl groups, $R^9$, $R^{10}$, $R^{11}$ and $R^{12}$ are each independently hydrogen, alkyl, alkenyl, alkoxy, aryl or aralkyl groups. The hydrocarbon radical may be bridged cycloaliphatically or aromatically via the Z fragment and Z may be either a divalent alkylene or alkenylene radical, with the proviso that the fragments with the indices d, e, f and/or h are freely permutable with one another, i.e. are exchangeable for one another within the polyether chain and, as desired, are distributed randomly or may be present successively in blocks, and hence are exchangeable for one another in the sequence within the polymer chain.

Preference is given to those silyl polyethers 1 in which the sum of the fragments d to j is greater than or equal to 3 when $R^1$ consists only of one monomer or oligomer.

The compounds of the formula (1) are referred to hereinafter as silyl polyethers 1, even if the structure may not include the features of a polymeric ether in the customary sense. However, the structural correlation of polyether structural elements with those of the silyl polyethers 1 is distinctly and clearly evident to the person skilled in the art.

In the context of this invention, the term "polyether" encompasses polyethers, polyetherols, polyetheralcohols, polyetheresters, but also polyethercarbonates, which may be used synonymously with one another. It is not required that the expression "poly" must be associated with a multitude of ether functionalities or alcohol functionalities in the molecule or polymer. Instead, this indicates merely that at least repeat units of individual monomer units or else compositions which have a higher molar mass and additionally also a certain polydispersity are present.

The word fragment "poly" in connection with this invention does not exclusively encompass compounds with at least 3 repeat units of one or more monomers in the molecule, but especially also those compositions of compounds which have a molecular weight distribution and possess a mean molecular weight of at least 200 g/mol. This definition takes account of the fact that it is customary in the field of industry in question already to refer to such compounds as polymers even if they do not appear to satisfy a polymer definition analogously to OECD or REACH guidelines (e.g. European Regulation No. 1907/2006).

$R^1$ is a fragment which originates from the starter or the starter compounds for the alkoxylation reaction, of the formula (3)

$$R^1\text{---}H \quad\quad (3)$$

(the H belongs to the OH group of an alcohol or of a phenolic compound), it being possible to use starters of the formula (3) alone or in mixtures with one another, which have at least one reactive hydroxyl group; the starter may thus also be water.

The OH-functional starter compounds $R^1$—H (3) used are preferably compounds with molar masses of 18 (water) to 10 000 g/mol, especially 50 to 2000 g/mol, and having 1 to 8, preferably having 1 to 4, hydroxyl groups.

The starters of the formula (3) used are preferably those in which $R^1$ is a hydroxyl group or a saturated or unsaturated, linear, branched or cyclic or further-substituted oxyorganic radical having 1 to 1500 carbon atoms, which may optionally also be interrupted by heteroatoms such as O, S, Si or N, or a radical containing an oxyaromatic system; $R^1$ is preferably an alkoxy, arylalkoxy or alkylarylalkoxy group and especially a polyether radical, in which the carbon chain may be interrupted by oxygen atoms, or a singularly or multiply fused oxyaromatic group or an optionally branched silicone-containing organic radical.

In addition, $R^1$—H may be an oxyalkyl-functional siloxane or an oxy-functional polyethersiloxane.

The chain length of the polyether radicals which have alkoxy, arylalkoxy or alkylarylalkoxy groups and are useable as starter compounds is as desired. The polyether, alkoxy, arylalkoxy or alkylarylalkoxy group preferably contains 1 to 1500 carbon atoms, more preferably 2 to 300 carbon atoms, especially 2 to 100 carbon atoms.

The compounds of the formula (3) are preferably selected from the group of the alcohols, polyetherols or phenols. Preference is given to using, as the starter compound, a mono- or polyhydric polyether alcohol or alcohol $R^1$—H (the H belongs to the OH group of the alcohol or phenol), or else water.

It is advantageous to use low molecular weight polyetherols having 1 to 8 hydroxyl groups and molar masses of 50 to 2000 g/mol, which have in turn been prepared beforehand by DMC-catalysed alkoxylation, as starter compounds (3). Examples of compounds of the formula (3) include water, allyl alcohol, butanol, octanol, dodecanol, stearyl alcohol, 2-ethylhexanol, cyclohexanol, benzyl alcohol, ethylene glycol, propylene glycol, di-, tri- and polyethylene glycol, 1,2-propylene glycol, di- and polypropylene glycol, 1,4-butanediol, 1,6-hexanediol, trimethylolpropane, glycerol, pentaerythritol, sorbitol, cellulose sugar, lignin or else further compounds which bear hydroxyl groups and are based on natural substances. In addition to compounds with aliphatic and cycloaliphatic OH groups, suitable compounds are any having 1 to 20 phenolic OH functions. These include, for example, phenol, alkyl- and arylphenols, bisphenol A and novolacs.

The compounds thus prepared give the synthetic freedom to select between polyoxyalkylene compounds having alkoxysilyl groups, which have alkoxysilyl functions in terminal positions, in isolated form, in cumulated blocks or else scattered in random distribution in the polyoxyalkylene chain.

The silyl polyethers 1 of the formula (1) are notable in that they can be prepared in a controlled and reproducible manner with regard to structure and molar mass. The sequence of the monomer units can be varied within wide limits. Epoxide monomers may be incorporated into the polymer chain in any desired block sequence or randomly. The fragments inserted into the polymer chain which forms by the reaction with ring opening of the reaction components are freely permutable with one another in their sequence, with the restriction that cyclic anhydrides and carbon dioxide are present in the polyether structure inserted randomly, i.e. not in homologous blocks.

Silyl polyethers of the formula (1) consist of alkoxysilyl-substituted chains which are highly functionalized in a controlled manner through the selection of the fragments d to j, according to the fragments inserted into the polymer chain by the reaction with ring opening of the reaction components, and hence can be tailored to different fields of use.

The indices shown in the formulae cited here and the value ranges for the indices specified are therefore understood as the mean values of the possible statistical distribution of the structures actually present and/or mixtures thereof. This is also true of structural formulae shown in exact terms as such, for example of formula (1) and/or (3).

According to the epoxy-functional alkoxysilane used and any further monomers used, and possibly also carbon dioxide, it is possible to obtain ester- or carbonate-modified silyl polyethers. The alkoxysilyl unit in the compound of the formula (1) is preferably a trialkoxysilyl unit.

As $^{29}$Si NMR and GPC studies show, the process-related presence of chain-terminal OH groups gives rise to the possibility of transesterification reactions on the silicon atom both during the DMC-catalysed preparation and, for example, in a subsequent process step. In formal terms, it is possible to exchange the alkyl radical R bonded to the silicon via an oxygen atom for a long-chain modified alkoxysilyl polymer radical. Bimodal and also multimodal GPC curves demonstrate that the alkoxylation products, in addition to the non-transesterified species as shown in formula (1), are those with double, in some cases triple or even many times the molar mass. Formula (1) therefore shows the complex chemical reality only in simplified form.

The silyl polyethers 1 are thus compositions which also comprise compounds in which the sum of the indices (a) plus (b) in formula (1) is less than 3 on statistical average, since some of the OR groups may be replaced by silyl polyether groups. The compositions thus contain species which are formed on the silicon atom with elimination of R—OH and condensation reaction with the reactive OH group of a further molecule of the formula (1). This reaction can proceed repeatedly until, for example, all RO groups on the silicon have been exchanged for further molecules of the formula (1). The presence of more than one signal in typical $^{29}$Si NMR spectra of these compounds supports the presence of silyl groups with different substitution patterns.

The values and preferred ranges specified for the indices (a) to (j) are thus also understood merely as average values over the different species which cannot be considered individually. The variety of chemical structures and molar masses is also reflected in broad molar mass distributions, which are typical of silyl polyethers 1 and completely unusual for conventional DMC-based polyethers, of $M_w/M_n$ usually ≥1.5.

In the prior art methods, only silyl-terminated prepolymers can be formed. The silyl polyethers 1 used in accordance with the invention as the reactive component differ from oligomers or polymers modified by conventional methods in that the controlled chain formation and the variable insertion of functional groups in a blockwise but also isolated manner forms structures which have both a silyl functionalization in scattered or blockwise form distributed over the entire chain and may additionally but not necessarily also bear a silyl functionalization at the termini.

Inextricably linked to the process for alkoxylation of epoxy-functional alkoxysilanes, detailed in the document DE 10 2008 000360.3 which is yet to be published, is the special feature that an OH functionality originating from the epoxy ring opening of the last epoxy monomer in each case with attachment to the OH-functional end of the growing chain is always present at the termini. Specifically this terminal OH functionality of the silyl polyethers used as reactive components here opens up the further functionalization thereof with compounds having isocyanate groups to form a urethane linkage.

Suitable isocyanate-containing compounds are all known isocyanates. Preference is given in the context of the inventive teaching, for example, to aromatic, aliphatic and cycloaliphatic polyisocyanates with a number-average molar mass of less than 800 g/mol. Examples of suitable compounds include diisocyanates from the group of 2,4-/2,6-toluene diisocyanate (TDI), methyldiphenyl diisocyanate (MDI), triisocyanatononane (TIN), naphthyl diisocyanate (NDI), 4,4'-diisocyanatodicyclohexylmethane, 3-isocyanatomethyl-3,3,5-trimethylcyclohexyl isocyanate (isophorone diisocyanate=IPDI), tetramethylene diisocyanate, hexamethylene diisocyanate (HDI), 2-methylpentamethylene diisocyanate, 2,2,4-trimethylhexamethylene diisocyanate (THDI), dodecamethylene diisocyanate, 1,4-diisocyanato-cyclohexane, 4,4'-diisocyanato-3,3''-dimethyldicyclohexyl-methane, 4,4'-diisocyanato-2,2-dicyclohexylpropane, 3-isocyanatomethyl-1-methyl-1-isocyanatocyclohexane (MCI), 1,3-diisooctylcyanato-4-methylcyclohexane, 1,3-diisocyanato-2-methylcyclohexane and α,α,α',α'-tetramethyl-m- or -p-xylylene diisocyanate (TMXDI), and mixtures consisting of these compounds.

Preferred starting materials for the preparation of the urethane-containing compounds are hexamethylene diisocyanate (HDI), isophorone diisocyanate (IPDI) and/or 4,4'-diisocyanatodicyclohexylmethane.

Likewise suitable as isocyanate-containing starting components are reaction products of the aforementioned isocyanates with themselves or with one another to give uretdiones or isocyanurates. Examples include Desmodur® N3300, Desmodur® N3400 or Desmodur® N3600 (all BayerMaterialScience, Leverkusen, Germany).

Additionally suitable are also derivatives of isocyanates, such as allophanates or biurets. Examples include Desmodur® N100, Desmodur® N75MPA/BA or Desmodur® VPLS2102 (all BayerMaterialScience, Leverkusen, Germany).

When such polyisocyanates are reacted with silyl polyethers which have more than one reactive OH group in the molecule, linear or branched copolymers are formed, in which the silyl polyether and isocyanate fragments are present in alternation joined to one another via urethane groups. When the isocyanate component is used in a molar excess based on the silyl polyether component, this forms terminally NCO-bearing reactive prepolymers with an additional alkoxysilyl functionality.

The invention therefore further provides a process for preparing urethanized polyols with terminal isocyanate groups, in which the reaction is performed with a molar excess of component (a) based on component (b).

In a particular embodiment of the present invention, further reaction at the urethane groups with isocyanates present in molar excess thus makes it possible to form allophanate structures, which allows additional branches to be incorporated into the structure of the prepolymers.

The invention thus further provides a process for preparing alkoxysilyl-modified allophanates, in which the isocyanate component (component (a)) is used in a molar excess based on component (b).

In a further embodiment of the present invention, it is possible, on the other hand, when using an excess of the silyl polyether, to prepare urethanized polyols which bear alkoxysilyl groups and have terminal OH groups.

The invention therefore further provides a process for preparing urethanized polyols with terminal OH groups, in which the reaction is performed with a molar excess of component (b) based on component (a), preferably the silyl polyether 1.

The silyl polyethers 1 can also be modified with monofunctional isocyanates by the process according to the invention. In the simplest case, alkyl, aryl or arylalkyl isocyanates are reacted with the OH groups of the silyl polyether to form the particular adduct and the reactive chain end of the silyl polyether used is simultaneously end-capped. Suitable examples for this purpose are methyl, ethyl, butyl, hexyl, octyl, dodecyl and stearyl isocyanate. Particularly suitable monofunctional isocyanates are those which in turn bear crosslinkable alkoxysilyl groups in the molecule. These preferably include isocyanatoalkyl-trialkoxysilanes and isocyanatoalkylalkyldialkoxysilanes.

Suitable alkoxysilane-functional monoisocyanates used may be isocyanatotrimethoxysilane, isocyanatomethyltriethoxy-silane, (isocyanatomethyl)methyldimethoxysilane, (isocyanatomethyl)methyldiethoxysilane, 3-isocyanatopropyltrimethoxysilane, 3-isocyanatopropylmethyldimethoxysilane, 3-isocyanatopropyltriethoxysilane and 3-isocyanatopropyl-methyldiethoxysilane. Preference is given here to the use of 3-isocyanatopropyltrimethoxysilane and -triethoxysilane.

By this chemical route, it is possible to obtain modified silyl polyethers supplemented terminally by an additional alkoxysilyl group in each case. The reaction of the alkoxysilane-functional monoisocyanates has to date been known only for conventional OH-functional polymers such as polyethers which themselves do not have any alkoxysilyl groups. Such products and processes are described, for example, in the documents cited hereinafter.

JP 11021463 is directed to a process for preparing trialkoxysilyl-terminated polyoxyalkylene ethers which derive from glycerol as the trifunctional alcohol, by modifying the particular glycerol polyethertriols with isocyanate-bearing trialkoxysilanes to form urethane bonds.

The patent JP 8295805 claims a process comparable in essence, which comprises the trialkoxysilyl modification of dipropylene glycol polyetherdiols prepared via DMC catalysis with isocyanate-bearing trialkoxysilanes.

A completely surprising observation to the person skilled in the art is the fact that the inventive polyurethane prepolymers which derive from the reaction of silyl polyethers of the formula (1) with isocyanate-containing compounds have surprisingly low viscosities in direct comparison with prior art compounds of analogous molecular weight, as specified, for example, for the Desmoseal® products in a brochure from Bayer MaterialScience with the title "Prepolymers: Products and Applications", Viscosities of 35 000 mPas are reported there. Surprisingly low means here low viscosity if compared to commercial urethanized silylpolethers of analogous molar mass and silyl functionality. For some reaction products as mentioned in the examples which have high viscosity NO comparable products are available as to the state of the art which would make any sense with respect to viscosity comparison.

The novel systems and compounds described here can be reacted with further reactive components to give copolymers. The stoichiometric ratio of the NCO component and of the OH component is crucial for the possible further reactions. For instance, it is possible to obtain reaction products by reacting one or more silyl polyethers 1 with further reactive components, especially those which possess functional groups with protic hydrogen, for example with one or more polyfunctional isocyanates and additionally further substances with isocyanate-reactive and/or with one or more hydroxyl-reactive compounds.

For example, it is possible in this way to introduce hydroxyl compounds, for example water, mono- or polyhydric alcohols, amines, thiols, alkoxysilanes, aminoalkoxysilanes, organic acid chlorides, isocyanates, diisocyanates, polyisocyanates, organic alkoxylates, organofluorine hydroxyl compounds, especially organofluorine hydroxyl compounds, etc., as an at least third component, before, during or after the reaction described as the primary reaction, in order thus to establish or to emphasize particular properties of the prepolymer. In this manner, it is optionally possible to introduce further functional groups into the molecule.

It is also thus possible to influence the molar mass and/or the viscosity of the products in a controlled manner. For instance, mean molar masses can be achieved within a wide range from 500 g/mol to more than 100 000 g/mol.

Further substances with isocyanate-reactive groups are, for example, mono- or polyfunctional alcohols, such as methanol, ethanol, butanol, glycerol, trimethylolpropane, 2-ethylhexyl alcohol or fluorinated alcohols such as 2,2,2-trifluoroethanol, diols, polyols or acrylated alcohols such as hydroxyethyl acrylate, hydroxypropyl acrylate, hydroxybutyl acrylate, or polyetherdiols or polyesterdiols or polytetrahydrofuran, and likewise silicone polyether copolymers which have OH-functional polyether radicals.

Further substances with isocyanate-reactive groups are, for example, all mono-, di- and polyamines such as stearylamine, ethylamine, isophoronediamine and amino-functional polymers such as polyethers and polysiloxanes, or diethanolamine, aminoalkoxysilanes, for example 3-amino-propyltrialkoxysilanes.

The invention therefore further provides a process for preparing urethane-containing prepolymer compositions comprising reaction products formed from silyl polyethers 1 according to the document DE 10 2008 000360.3, which is yet to be published, with isocyanate-bearing compounds.

The invention further provides a process for preparing urethane-containing silylated polymers, characterized in that one or more isocyanates are reacted with one or more silyl polyethers 1 in the temperature range from −15° C. to 220° C., preferably between +15° C. and 180° C. and especially between +30 and 150° C.

To prepare the prepolymer compositions, one or more silyl polyethers 1 are combined with one or more isocyanates and optionally reacted with further substances having isocyanate-reactive and/or hydroxyl-reactive groups at −15° C. to 220° C., preferably between +15° C. and 180° C. and especially between +30 and 150° C., optionally in the presence of a catalyst. In some cases, it may be advisable to add one or more solvents or other nonreactive components, for example fillers, emulsifiers and/or defoamers.

The reaction can be performed in monophasic form in solution or in the polyphasic system of an emulsion and/or suspension.

Suitable solvents are, for example, aromatic solvents such as toluene or xylene, aliphatic solvents such as pentane or cyclohexane, or ethers, for example THF.

Suitable emulsifiers are, for example, alkoxylated fatty alcohols or polyethersiloxanes.

In the course of performance of the process according to the invention, the silyl polyether(s) can be added to the isocyanate(s), or vice versa. The variation in the metering sequence of the individual components allows the reaction to be controlled. In addition, continuous reactors are also suitable for preparing the inventive urethane-containing silylated polymers.

Frequently, it is advisable to stir the mixture of the reactants during the reaction phase, but other methods for mixing, for example pumped circulation, would also be appropriate.

The reaction conditions under which the silyl polyethers 1 are reacted with isocyanates depend on a series of different parameters. For instance, aromatic isocyanates generally have a higher reactivity compared to aliphatic isocyanates, which leads to higher reaction temperatures being needed for reaction in the case of aliphatic isocyanates. The reaction rate depends, for example, on the temperature, the nature of the reactants, the presence of a catalyst and the presence of a solvent. The reaction conditions, however, also influence the product properties since, according to conditions, side reactions, for example allophanate formation, take place to different degrees.

In some cases, it is advisable to alter the temperature during the reaction and, for example, to select a temperature profile.

There is a series of catalysts which are suitable for the acceleration of the reaction of isocyanates and silyl polyethers 1. For example, it is possible to use amines such as 1,4-diazabicyclo[2.2.2]octane, N,N-diethylcyclo-hexylamine, N-methylmorpholine, N,N,N',N'-tetramethyl-methanediamine, tetraalkylammonium compounds, N,N,N-trimethyl-N-2-hydroxypropylammonium hydroxide, N,N,N-tri-methyl-N-2-hydroxypropylammonium 2-ethylhexanoate, choline 2-ethylhexanoate, or metal compounds such as di-n-butyltin dilaurate, tin octoate, tin 2-ethylhexanoate, zinc octoate, zinc 2-ethylhexanoate, zinc acetylacetonate, zinc 2-ethylcaproate, bismuth nitrate, lead 2-ethylhexanoate, iron chloride, tetrabutyl titanate or bismuth octoates, alone or in any desired mixtures with one another. In many cases, a synergistic effect is also found when two different catalysts are used together. Suitable mixtures of catalysts are, for example, the combination of dibutyltin laurate and tetramethylbutanediamine, tin octoate and tetramethylbutanediamine or tin octoate and 1,4-diazabicyclo[2.2.2]octane. Additionally suitable are Lewis acids as catalysts. The catalyst content is 0.0001 to 10% by weight, preferably in the range from 0.001 to 5% by weight, based in each case on the amount of silyl polyether used. In the course of the process according to the invention, some or all of the OH functions of the silyl polyethers 1 are reacted with isocyanate groups.

If polymers which still have reactive NCO groups are to be prepared, it is necessary to use at least one polyfunctional isocyanate and not to completely convert the NCO functionalities, or to use an excess of NCO functions based on the OH functions. In some cases, it should be noted that some of the NCO functions are converted by side reactions, for example in the formation of allophanates.

Further substances with isocyanate-functional groups can be added as early as during the reaction of the silyl polyethers 1 with at least one polyfunctional isocyanate in order also to incorporate them directly into the polymer. They can, however, also be reacted with excess isocyanate groups after the reaction of the silyl polyethers 1 with at least one polyfunctional isocyanate.

When the isocyanate component is used in stoichiometric excess over the OH groups of the silyl polyether 1, prepolymers which simultaneously bear NCO and alkoxysilyl groups are obtained. Such dual-cure systems can be made to cure by two different mechanisms with graduated reactivity.

The inventive compositions comprising urethanized and silylated polymers may contain further components bearing reactive groups. These include all compounds with at least one isocyanate, hydroxyl, epoxy and unsaturated C=C group, for example acrylates, methacrylates, vinyl and allyl compounds.

The invention therefore further provides compositions comprising at least one or more than one inventive (prepolymeric) urethane-containing reaction product and further compounds with at least one isocyanate, hydroxyl, epoxy and unsaturated C=C group, for example acrylates, methacrylates, vinyl or allyl compounds and/or reactive silanes or silyl-functional compounds.

Further conversion products which are obtainable from the compositions and which then possess, for example, urea groups, biuret structures or allophanate structures are explicitly also included.

The reactive silanes present in the inventive compositions may, for example, be others, preferably alkoxysilanes. These alkoxysilanes may be either monomeric silanes such as those of the formula (4) or polymer-bound silanes

$$U_xSiV_{(4-x)} \qquad (4)$$

where U represents identical or different groups not hydrolysable in the presence of water and catalytic amounts of Brønsted acid at temperatures up to 100° C., V represents identical or different groups hydrolysable in the presence of water and catalytic amounts of Brønsted acid at temperatures up to 100° C., or hydroxyl groups, and x is 1, 2, 3 or 4.

In the context of this invention, "hydrolysable" means that at least 80% of the groups can be hydrolysed and hence eliminated under the selected conditions.

The hydrolysable V groups are, for example, H, halogen, alkoxy, preferably methoxy, ethoxy, i-propoxy, n-propoxy or butoxy, aryloxy (preferably phenoxy), acyloxy, preferably acetoxy or propionyloxy, acyl, preferably acetyl, amino, monoalkylamino or dialkylamino groups. The unhydrolysable U radical may, for example, be an alkyl, alkenyl, alkynyl, aryl, alkylaryl or aralkyl radical. The alkyl chain may have 0 to 50, preferably 0 to 22, carbon atoms and may also be interrupted by heteroatoms such as oxygen or nitrogen or sulphur, or else may be a silicone radical. The aromatic radical may also be heteroaromatic. The U and V radicals may also have one or more customary substituents, for example halogen or alkoxy.

Unhydrolysable U radicals according to the formula (4) with functional groups can be selected from the range of the glycidyl or glycidyloxyalkylene radicals, for example β-glycidyloxyethyl, γ-glycidyloxypropyl, δ-glycidyloxypropyl, ε-glycidyloxypentyl, ω-glycidyloxyhexyl or 2-(3,4-epoxycyclohexyl)ethyl, the methacryloyloxyalkylene and acryloyloxyalkylene radicals, for example methacryloyl-oxymethyl, acryloyloxymethyl, methacryloyloxyethyl, acryloyloxyethyl, methacryloyloxypropyl, acryloyloxypropyl, methacryloyloxybutyl or acryloyloxybutyl, and the 3-iso-cyanatopropyl radical, and/or cyclic and/or linear (poly)urethane-containing and/or urea-containing and/or (poly)amino-containing radical.

Particularly widespread is the use of low-viscosity, monomeric compounds bearing trimethoxysilyl and triethoxysilyl groups, which are capable in the presence of air humidity and suitable catalysts, usually even at room temperature, of condensing with one another to eliminate alkoxy groups and form Si—O—Si bonds. Such organofunctional monomeric silanes are, for example, N-cyclohexylamino-methyltrimethoxysilane, N-cyclohexyl-3-aminopropyltrieth-oxysilane, 3-aminopropyltrimethoxysilane, vinyltrimeth-oxysilane, vinyltriethoxysilane, vinyldimethoxymethyl-silane, 3-isocyanatopropyltrimethoxysilane, 3-glycidyl-oxypropyltrimethoxysilane, 3-glycidyloxypropyltriethoxy-silane, 3-methacryloyloxypropyltrimethoxysilane, methyltrimethoxysilane, methyltriethoxysilane, dimethyldimethoxysilane, phenyltriethoxysilane and hexadecyltrimethoxy-silane. The person skilled in the art is essentially aware of the methodology.

The inventive silylated polymers having urethane groups can likewise be used in mixtures or compositions with all silyl-functional compounds which have at least one alkoxysilyl group chemically bonded to a polymer structure. Such silane-modified polymers are silane compounds of the type of the formula (5)

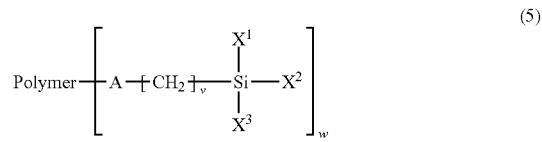

where
$X^2$, $X^2$ and $X^3$ are each independently alkyl or alkoxy radicals having 1-8 carbon atoms,
A is a radical containing a carboxyl, carbamate, amide, carbonate, ureido or sulphonate group, or is an oxygen atom,
w is an integer from 1 to 8 and
v is an integer from 1 to 20, preferably 1 to 15 and especially 1 to 5.

The polymer radical is selected from a group consisting of alkyd resins, oil-modified alkyd resins, saturated or unsaturated polyesters, natural oils, epoxides, polyamides, polycarbonates, polyethylenes, polypropylenes, polybutylenes, polystyrenes, ethylene-propylene copolymers, (meth)acrylates, (meth)acrylamides and salts thereof, phenol resins, polyoxymethylene homo- and copolymers, polyurethanes, polysulphones, polysulphide rubbers, nitrocelluloses, vinyl butyrates, vinyl polymers, ethylcelluloses, cellulose acetates and/or butyrates, rayon, shellac, waxes, ethylene copolymers, organic rubbers, polysiloxanes, polyethersiloxanes, silicone resins, polyethers, polyetheresters and/or polyethercarbonates.

The polymers of the formula (5) used preferentially in mixtures with the silyl polymers having urethane groups include so-called α-silane-terminated polymers, whose reactive alkoxysilyl groups are separated only by a methylene unit (v=1) from a nitrogen-containing polymer-bound A group, as described in WO 2005/100482 and EP-A1-1 967 550 (US 2009-088523).

Further silane polymers of the formula (5) usable in accordance with the invention in curable compositions are those in which the silane groups are bonded terminally via a propylene unit (v=3) to a polymer structure and in which A is a urethane group. Preference is given to polyalkylene oxides, especially polypropylene glycols (w=2), with silane functions on each of the two chain ends, as described in EP-A1-1 824 904 (US 2009-0264612).

Compounds of the formula (5) likewise suitable as mixture constituents are silane-terminated polyurethanes, the preparation of which from a polyol by reaction with a diisocyanate and then with an amino-functional alkoxysilane is described, for example, in U.S. Pat. No. 7,365,145, U.S. Pat. No. 3,627,722 or U.S. Pat. No. 3,632,557. The linking A group is a radical bearing urethane and urea groups.

Further polymers usable in the context of the invention are urethane- and urea-free silyl-terminated polyethers of the formula (5) where A is oxygen, in which the terminal alkoxysilyl groups are attached directly to the polymer structure via an ether function. Such silyl polymers are described in U.S. Pat. No. 3,971,751. They consist preferably of a polyether base structure where v in formula (5) preferably has the value of 3 and w preferably has the value of 2, and are obtainable as MS Polymer© products from Kaneka.

It is also possible to combine polysiloxanes bearing alkoxysilyl groups, as described, for example, in WO 2007/061847 (US 2008-0306208), with the inventive urethanized and silylated polymers.

It is generally left to the expert to select the components suitable for the desired profile of properties, in order to obtain optimized copolymer systems. The inventive compositions therefore provide a construction kit of different profiles of properties, from which an optimized assembly can be selected according to the application.

The inventive introduction of urethane groups into the prepolymer structure permits the good adhesion properties on various substrates, the high resistance to solvents, chemicals and weathering influences and the high mechanical flexibility, which are known from the pure polyurethanes, to be combined with the benefits of curable silyl polyethers.

It is surprising here that even urethanized silyl polyether-isocyanate adducts provided with considerable alkoxysilyl functionalization density are usually low-viscosity liquids which are easy to handle, such that, even in the case that highly crosslinked adhesive bonds with good adhesion are desired, there are no observed restrictions whatsoever with regard to the metered addition of this component. This observation differentiates the inventive teaching from the procedure detailed in WO 2008/058955 (US 2010-078117), which is directed to the introduction of free silane monomers as formulation constituents into the final formulations, in order to ensure that the necessary crosslinking density is achieved with simultaneously low processing viscosity. The prepolymers having alkoxysilyl groups, which can barely be delimited with regard to their structural variety, already open up to the person skilled in the art and familiar with polymer chemistry, through the incorporation, for example, of ester, carbonate and aromatic structural elements, a freedom of configuration which addresses virtually any performance requirements.

Further subjects of the invention are described by the claims, the full disclosure-content of which forms part of this description.

The inventive urethane-containing silylated reaction products and prepolymers and the process for preparation thereof are described hereinafter by way of example, though the invention cannot be considered to be restricted to these illustrative embodiments.

When ranges, general formulae or compound classes are specified hereinafter, these shall include not only the corresponding ranges or groups of compounds which are mentioned explicitly but also all sub-ranges and sub-groups of compounds which can be obtained by selecting individual values (ranges) or compounds.

BRIEF DESCRIPTION OF THE DRAWINGS

FIG. 1 is a larger depiction of the silyl polyether 1 of the formula (1).

The invention is further described by the following non-limiting examples which further illustrate the invention, and are not intended, nor should they be interpreted to, limit the scope of the invention.

WORKING EXAMPLES

In the examples which follow, the following silyl polyethers 1 containing trialkoxysilyl groups were used, which have been prepared according to the as yet unpublished document DE 10 2008 000360.3 by the process principle of DMC-catalysed alkoxylation of 3-glycidyloxy-propyltriethoxysilane (Dynasylan® GLYEO) from Evonik Degussa GmbH. PO means propylene oxide.

GPC measurements to determine the polydispersity and mean molar masses were carried out under the following analysis conditions: column combination SDV 1000/10 000 Å (length 65 cm), temperature 30° C., THF as mobile phase, flow rate 1 ml/min, sample concentration 10 g/l, RI detector, evaluation against polypropylene glycol standard.

The viscosities were measured on the basis of DIN 53019 with a rotational viscometer from Brookfield (model LVT) at 25° C.

The NCO content in percent was determined via back-titration with 0.1 molar hydrochloric acid after reaction with butylamine according to DIN EN ISO 11909.

Trialkoxysilyl Polyether SP-1:
Almost colorless, low-viscosity silyl polyether with four-fold trialkoxysilane functionality
Chemical Structure According to Monomer Dosage:
polypropylene glycol monobutyl ether (400 g/mol)+2 mol PO+(21 mol PO/4 mol GLYEO randomly)+2 mol PO, theoretical mean molar mass 3090 g/mol,
mean molar mass $M_w$ 2760 g/mol, polydispersity $M_w/M_n$ 1.38, viscosity (25° C.) 365 mPa*s.

Trialkoxysilyl Polyether SP-2:
Almost colorless, low-viscosity silyl polyether with four-fold trialkoxysilane functionality
Chemical Structure According to Monomer Dosage:
polypropylene glycol (2000 g/mol)+17 mol PO+(103 mol PO/4 mol GLYEO randomly), theoretical molar mass 10 000 g/mol,
mean molar mass $M_w$ 10 900 g/mol, polydispersity $M_w/M_n$ 2.16, viscosity (25° C.) 5050 mPa*s.

Trialkoxysilyl Polyether SP-3:
Almost colorless, low-viscosity silyl polyetherester with four-fold trialkoxysilane functionality
Chemical Structure According to Monomer Dosage:
polypropylene glycol (700 g/mol)+6 mol hexahydrophthalic anhydride+10 mol PO+4 mol GLYEO (blockwise)
mean molar mass $M_w$ 3400 g/mol, viscosity (25° C.) 5000 mPa*s.

Trialkoxysilyl Polyether SP-4:
Low molecular weight, octanol-started, almost colorless and low-viscosity polyether of blockwise structure with seven-fold trialkoxysilane functionality
Chemical Structure According to Monomer Dosage:
1-octanol+8 mol PO+3.5 mol GLYEO+8 mol PO+3.5 mol GLYEO+2 mol PO mean molar mass 3100 g/mol, OH number 19.5 mg KOH/g, viscosity (25.0° C.): 190 mPa·s.

To calculate the amounts, the theoretical molar mass of the trialkoxysilyl polyethers was employed.

Example 1

Preparation of an NCO- and Urethane-Containing Silyl Polyether 150.2 g (49 mmol corresponds to 49 mmol of OH functions) of the silyl polyether SP-1 were initially charged in a 250 ml three-neck flask with reflux condenser, thermometer and precision glass stirrer. Subsequently, 10.8 g of isophorone diisocyanate—IPDI (49 mmol corresponds to 98 mmol of NCO functions) were metered in gradually at room temperature and the mixture was admixed with 0.08 g of dibutyltin dilaurate. The reaction mixture was heated to 60° C. and stirred at this temperature for one hour. This gave a clear product with a viscosity of 760 mPa s and an NCO value of w(NCO)=1.26%.

The starting weight of the isophorone diisocyanate was selected such that the NCO groups are present in excess based on the OH groups of the silyl polyether SP-1, such that products which, as well as the alkoxysilyl groups, also bear free NCO groups are formed.

Example 2

Preparation of a Urethane-Containing Silyl Polyether 100 g of the silyl polyether SP-1 (32 mmol corresponds to 32 mmol of OH functions) were initially charged in a 250 ml three-neck flask with reflux condenser, thermometer and precision glass stirrer. Subsequently, 3.6 g of isophorone diisocyanate (16 mmol corresponds to 32 mmol of NCO functions) were metered in gradually at room temperature and the mixture was admixed with 0.05 g of dibutyltin dilaurate. The reaction mixture was heated to 60° C. and stirred at this temperature for two hours. This gave a clear product with a viscosity of 880 mPa*s and an NCO value of w(NCO)=0%.

The starting weight of the isophorone diisocyanate was selected such that the OH groups of the silyl polyether are present in an equimolar ratio to the NCO functions, such that polyethers are joined to one another and high molecular weight polyethers are formed.

Example 3

Preparation of a Urethane-Containing Silyl Polyether with an Alkyl End Group 100 g of the silyl polyether SP-1 (32 mmol corresponds to 32 mmol of OH functions) were initially charged in a 250 ml three-neck flask with reflux condenser, thermometer and precision glass stirrer. Subsequently, 9.56 g of stearyl isocyanate (32 mmol corresponds to 32 mmol of NCO functions) were metered in gradually at room temperature and the mixture was admixed with 0.05 g of dibutyltin dilaurate. The reaction mixture was heated to 100° C. and stirred at this temperature for one hour. This gave a product which is cloudy at room temperature and has a viscosity of 455 mPa*s and an NCO value of w(NCO)=0%.

The starting weight of the stearyl isocyanate was selected such that the OH groups of the silyl polyether are present in an equimolar ratio to the NCO functions, such that the OH groups are very substantially consumed and the polyethers are modified with a stearyl group.

Example 4

Preparation of a Urethane-Containing Silyl Polyether with a Triethoxysilyl End Group 100 g of the silyl polyether SP-1 (32 mmol corresponds to 32 mmol of OH functions) were initially charged in a 250 ml three-neck flask with reflux condenser, thermometer and precision glass stirrer. Subsequently, 8.0 g of 3-isocyanatopropyltriethoxysilane (32 mmol corresponds to 32 mmol of NCO functions) were metered in gradually at room temperature. The mixture was heated to 80° C. and admixed with 0.05 g of dibutyltin dilaurate. The reaction mixture was stirred at this temperature for one hour. This gave a product which was clear at room temperature and had a viscosity of 800 mPa*s and an NCO value of w(NCO)=0%.

The starting weight of the isocyanatopropyltriethoxysilane was selected such that the OH groups of the silyl polyether are present in an equimolar ratio to the NCO functions, such that the OH groups are very substantially consumed and the polyethers are modified with further triethoxysilyl groups.

Example 5

Preparation of a Urethane-Containing Silyl Polyether with Desmodur N 3300

100 g of the silyl polyether SP-1 (32 mmol corresponds to 32 mmol of OH functions) were initially charged in a 250 ml three-neck flask with reflux condenser, thermometer and precision glass stirrer. Subsequently, 6.25 g of Desmodur N 3300 (w(NCO)=21.8% corresponds to 32 mmol of NCO functions) from Bayer (aliphatic polyisocyanate, HDI trimer) were metered in gradually at room temperature. The mixture was heated to 80° C. and admixed with 0.05 g of dibutyltin dilaurate. An exothermic reaction set in, in the course of which the reaction mixture heated up to 105° C. The reaction mixture was subsequently stirred at 80° C. for one hour. This gave a product which was clear at room temperature and had a viscosity of 1665 mPa*s and an NCO value of w(NCO)=0%.

The starting weight of the Desmodur® N 3300 was selected such that the OH groups of the silyl polyether are present in an equimolar ratio to the NCO functions, such that the OH groups are very substantially consumed and polyethers are joined to one another, so as to form a branched silyl polyether.

Example 6

Preparation of a Urethane-Containing Silyl Polyether with IPDI—Isophorone Diisocyanate 100 g of the silyl polyether SP-2 (10 mmol corresponds to 20 mmol of OH functions) were initially charged in a 250 ml three-neck flask with reflux condenser, thermometer and precision glass stirrer. Subsequently, 1.48 g of Vestanat IPDI (6.7 mmol corresponds to 13.4 mmol of NCO functions) from Evonik Degussa GmbH (aliphatic isocyanate) were metered in gradually at room temperature. The mixture was heated to 80° C. and admixed with 0.05 g of dibutyltin dilaurate. The reaction mixture was subsequently stirred at 80° C. for one hour. This gave a product which was clear at room temperature with a viscosity of 21 750 mPa*s and an NCO value of w(NCO)=0%.

The starting weight of the Vestanat® IPDI was selected such that the OH groups of the silyl polyether are present in excess based on the NCO functions, such that a plurality of polyethers are joined to one another, and a high molecular weight block polyether is accordingly formed.

Example 7

Preparation of a Urethane- and Isocyanate-Containing Silyl Polyether with IPDI 150 g of the silyl polyether SP-2 (15 mmol corresponds to 30 mmol of OH functions) were initially charged in a 250 ml three-neck flask with reflux condenser, thermometer and precision glass stirrer. Subsequently, 4.45 g (20 mmol corresponds to 40 mmol of NCO functions) of Vestanat® IPDI from Evonik Degussa GmbH (aliphatic isocyanate) were metered in gradually at room temperature. The mixture was heated to 60° C. and admixed with 0.07 g of dibutyltin dilaurate. The reaction mixture was subsequently stirred at 60° C. for one hour. This gave a product which was clear at room temperature and had a viscosity of 184 000 mPa*s and an NCO value of w(NCO)=0.23%.

The starting weight of the Vestanat® IPDI was selected such that the OH groups of the silyl polyether are present in deficiency based on the NCO functions, such that some of the NCO functions remain, and polymers which bear both NCO and alkoxysilyl groups are accordingly formed.

Example 8

Preparation of a Urethane- and Isocyanate-Containing Silyl Polyether with IPDI 150 g of the silyl polyether SP-2 (15 mmol corresponds to 30 mmol of OH functions) were initially charged in a 250 ml three-neck flask with reflux condenser, thermometer and precision glass stirrer. Subsequently, 6.67 g of Vestanat® IPDI (30 mmol corresponds to 60 mmol of NCO functions) from Evonik Degussa GmbH (aliphatic isocyanate) were metered in gradually at room temperature. The mixture was heated to 60° C. and admixed with 0.08 g of dibutyltin dilaurate. The reaction mixture was subsequently stirred at 60° C. for one hour. This gave a product which was clear at room temperature with a viscosity of 16 000 mPa*s and an NCO value of w(NCO)=0.68%.

The starting weight of the Vestanat® IPDI was selected such that the OH groups of the silyl polyether are present in deficiency based on the NCO functions, such that some of the NCO functions remain, and polymers which bear both NCO and alkoxysilyl groups are accordingly formed.

Example 9

Preparation of a Urethane- and Isocyanate-Containing Silyl Polyether with IPDI 150 g of the silyl polyether SP-3 (45 mmol corresponds to 90 mmol of OH functions) were initially charged in a 250 ml three-neck flask with reflux condenser, thermometer and precision glass stirrer. Subsequently, 20.0 g of Vestanat® IPDI (90 mmol corresponds to 180 mmol of NCO functions) from Evonik Degussa GmbH (aliphatic isocyanate) were metered in gradually at room temperature. The mixture was heated to 60° C. and admixed with 0.09 g of dibutyltin dilaurate. An exothermic reaction set in, in the course of which the reaction mixture heated up to 66° C. The reaction mixture was subsequently stirred at 60° C. for one hour. This gave a clear product which was resinous at room temperature and had an NCO value of w(NCO)=2.1%.

The starting weight of the Vestanat® IPDI was selected such that the OH groups of the silyl polyether are present in deficiency based on the NCO functions, such that some of the NCO functions remain, and polymers which bear both NCO and alkoxysilyl groups are accordingly formed.

Example 10

Preparation of a Urethane-Containing Silyl Polyether with a Poly-THF Block with IPDI 8 g of polytetrahydrofuran (Terathane 1000 from Invista, polytetrahydrofuran with a mean molar mass of 1000 g/mol) were initially charged with 5.3 g of Vestanat® IPDI (24 mmol corresponds to 48 mmol of NCO functions) from Evonik Degussa GmbH (aliphatic isocyanate) and 0.13 g of dibutyltin laurate in a 500 ml three-neck flask with reflux condenser, thermometer and precision glass stirrer, and mixed. Subsequently, 20 g of the silyl polyether SP-2 were added. The mixture was heated to 60° C. and stirred for one hour. Subsequently, a further 220 g of the silyl polyether SP-2 were added, and the mixture was heated to 80° C. and stirred for a further hour. This gave a clear product with an NCO value of w(NCO)=0% and a viscosity of 31 500 mPa*s.

The starting weight of the Vestanat® IPDI was selected such that the OH groups of the silyl polyether and of the polytetrahydrofuran are present in deficiency based on the NCO functions, such that some of the OH functions remain, and polymers which bear both OH and alkoxysilyl groups are accordingly formed, and some of the polyether backbone consists of polytetrahydrofuran.

Example 11

Preparation of a Urethane-Containing Silyl Polyether with IPDI in the Presence of tetra-n-butyl Titanate 185 g of the silyl polyether SP-4 (theoretical molar mass 3086 g/mol, 60 mmol corresponds to 60 mmol of OH functions) were initially charged in a 250 ml three-neck flask with reflux condenser, thermometer and precision glass stirrer. Subsequently, 6.67 g (30 mmol corresponds to 60 mmol of NCO functions) of Vestanat® IPDI from Evonik Degussa GmbH (aliphatic isocyanate) were metered in gradually at room temperature. The mixture was admixed with 0.1 g of tetra-n-butyl titanate and heated to 120° C. The reaction mixture was subsequently stirred for seven hours. This gave an orange product which was clear at room temperature and had an NCO value of w(NCO)=0.04%.

The starting weight of the Vestanat® IPDI was selected such that the OH groups of the silyl polyether are present in an equimolar ratio based on the NCO functions, such that high molecular weight polymers are formed. It was additionally found that titanium compounds are also suitable catalysts.

Example 12

Preparation of a Urethane-Containing Silyl Polyether with IPDI in the Presence of Bismuth Catalysts 123 g of the silyl polyether SP-4 (theoretical molar mass 3086 g/mol, 40 mmol corresponds to 40 mmol of OH functions) were initially charged in a 250 ml three-neck flask with reflux condenser, thermometer and precision glass stirrer.

Subsequently, 4.45 g (20 mmol corresponds to 40 mmol of NCO functions) of Vestanat® IPDI from Evonik Degussa GmbH (aliphatic isocyanate) were metered in gradually at room temperature. Subsequently, 0.06 g of Tegokat 722 (bismuth octoate from TIB Chemicals, Germany) was added. The mixture was heated to 80° C. The reaction mixture was subsequently stirred for four hours. This gave a product which was clear at room temperature and had an NCO value of w(NCO)=0.08% and a viscosity of 385 mPa*s.

The starting weight of the Vestanat® IPDI was selected such that the OH groups of the silyl polyether are present in an equimolar ratio based on the NCO functions, such that high molecular weight polymers form. It was additionally found that bismuth compounds are also suitable catalysts.

Example 13

Preparation of a Urethane-Containing Silyl Polyether with IPDI in the Presence of Amines 123 g of the silyl polyether SP-4 (theoretical molar mass 3086 g/mol, 40 mmol corresponds to 40 mmol of OH functions) were initially charged in a 250 ml three-neck flask with reflux condenser, thermometer and precision glass stirrer. Subsequently, 4.45 g (20 mmol corresponds to 40 mmol of NCO functions) of Vestanat® IPDI from Evonik Degussa GmbH (aliphatic isocyanate) were metered in gradually at room temperature. Subsequently, 0.06 g of 1,4-diazabicyclo-[2.2.2]octane was added. The mixture was heated to 80° C. The reaction mixture was subsequently stirred for seven hours. This gave a product which was cloudy at room temperature and had a residual NCO value of w(NCO)=0.05%.

The starting weight of the Vestanat® IPDI was selected such that the OH groups of the silyl polyether are present in an equimolar ratio based on the NCO functions, such that high molecular weight polymers are formed. It was additionally found that amines are also suitable catalysts.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. Urethane-containing reaction products obtained by the reaction of:
   (a) at least one compound having one or more isocyanate groups, and bearing no alkoxysilyl and/or alkylsilyl groups; with
   (b) at least one compound bearing a plurality of alkoxysilyl groups and additionally bearing at least one hydroxyl group;
   (c) optionally in the presence of at least one catalyst;
   wherein the molecules of the reaction products have an average of more than one alkoxysilyl group per urethane group.

2. The reaction products according to claim 1;
   wherein the component (b) utilized is a compound of formula 1:

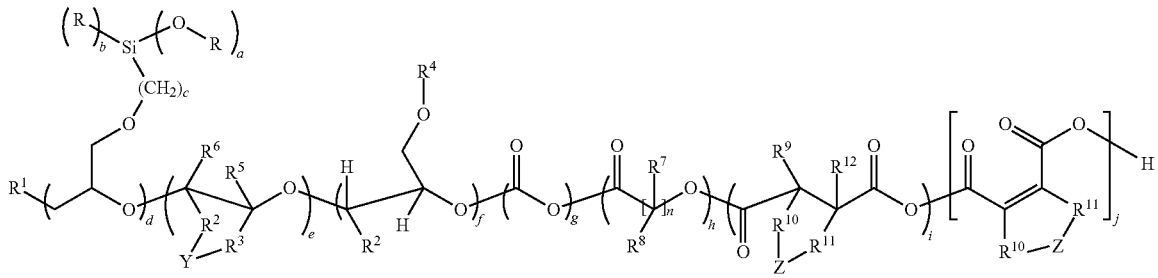

formula 1 where:
   a is an integer from 1 to 3; and
   b is an integer from 0 to 2;
   with the proviso that a sum of a plus b is 3;
where:
   c is an integer from 0 to 22;
   d is an integer from 2 to 500;
   e is an integer from 0 to 10,000;
   f is an integer from 0 to 1,000;
   g is an integer from 0 to 1,000;
   h, i, and j are each independently integers from 0 to 500;
   n is an integer from 2 to 8;
   Y is absent;
   R is independently one or more, identical or different, linear or branched, saturated, monounsaturated, or polyunsaturated, alkyl or haloalkyl radical having 1 to 20 carbon atoms;
   $R^1$ is:
      a hydroxyl group; or
      a saturated or unsaturated, linear, branched, or cyclic, substituted or unsubstituted, organic oxygen-containing radical having 1 to 1500 carbon atoms, where the carbon atoms are optionally interrupted by at least one hetero atom selected from the group consisting of O, S, Si, and N; or
      a radical comprising an aromatic oxygen-containing radical;
   $R^2$ and $R^3$ are each independently:
      H; or
      a linear or branched radical having 1 to 20 carbon atoms;
   $R^4$ is:
      a linear or branched alkyl radical of 1 to 24 carbon atoms; or
      an aromatic or cycloaliphatic radical which optionally bears alkyl groups;
   $R^5$ and $R^6$ radicals are each:
      H; or
      a monovalent hydrocarbon radical;

R⁷ and R⁸ are each independently:
   hydrogen; or
   alkyl, alkoxy, aryl, or aralkyl groups; and
R⁹ and R¹² are each independently:
   hydrogen; or
   an alkyl, alkenyl, alkoxy, aryl, or aralkyl group; and
R¹⁰ and R¹¹ are each independently:
   hydrogen; or
   an alkyl, alkenyl, alkoxy, aryl, or aralkyl group;
   where R¹⁰ and R¹¹ are optionally bridged cycloaliphatically or aromatically via the Z fragment; and
   where, if present, Z is a divalent alkylene or alkenylene radical;
wherein, optionally, at least two of the fragments with the indices d, e, f, and h are freely permutable with one another, are distributed randomly or successively in blocks, and hence are exchangeable for one another in the sequence within the polymer chain.

3. Reaction products according to claim 2;
wherein the compound of formula 1 is a silyl polyether where:
   e is an integer from 2 to 10,000.

4. A copolymer obtained by the reaction of:
the reaction products according to claim 1; with
at least one further component (d) reactive towards the reaction products.

5. The copolymer according to claim 4;
wherein component (d) comprises at least one compound with a functional group with protic hydrogen, selected from the group consisting of alcohols, amines, thiols, organofluorine hydroxyl compounds, alkoxysilanes, water.

6. A composition comprising:
at least one reaction product according to claim 1.

7. A composition comprising:
at least one urethane-containing reaction product according to claim 1; and
at least one additional compound selected from the group consisting of:
   compounds with at least one isocyanate, hydroxyl, epoxy, and/or unsaturated C=C group; and
   acrylates, methacrylates, vinyl compounds, allyl compounds, silanes, and silyl-functional compounds.

8. A composition comprising:
at least one urethane-containing reaction product according to claim 1; and
at least one additional compound;
wherein the at least one additional compound comprises a silane of the formula (4):

where:
   U represents identical or different groups not hydrolysable in the presence of water and catalytic amounts of Brønsted acid at temperatures up to 100° C.;
   V represents identical or different groups hydrolysable in the presence of water and catalytic amounts of Brønsted acid at temperatures up to 100° C., or hydroxyl groups; and
   X is 1, 2, or 3; and/or
wherein the at least one additional compound comprises a silyl-functional compound of the formula (5):

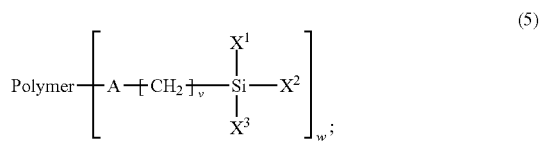

where:
   X¹, X², and X³ are each independently alkyl or alkoxy radicals having 1-8 carbon atoms;
   A is a radical containing a carboxyl, carbamate, amide, carbonate, ureido or sulphonate group, or is an oxygen atom,
   w is an integer from 1 to 8;
   v is an integer from 1 to 20; and
   "Polymer-" is selected from a group consisting of alkyd resins, oil-modified alkyd resins, saturated or unsaturated polyesters, natural oils, epoxides, polyamides, polycarbonates, polyethylenes, polypropylenes, polybutylenes, polystyrenes, ethylene-propylene copolymers, (meth)acrylates, (meth)acrylamides and salts thereof, phenol resins, polyoxymethylene homo- and copolymers, polyurethanes, polysulphones, polysulphide rubbers, nitrocelluloses, vinyl butyrates, vinyl polymers, ethylcelluloses, cellulose acetates, cellulose butyrates, rayon, shellac, waxes, ethylene copolymers, organic rubbers, polysiloxanes, polyethersiloxanes, silicone resins, polyethers, polyetheresters, and polyethercarbonates.

9. A process for preparing the reaction products according to claim 1, comprising:
reacting component (b) with component (a), to obtain the reaction products.

10. The process according to claim 9;
wherein a molar excess of component (a), based on component (b), is utilized in the reaction.

11. The process according to claim 10;
wherein alkoxysilyl-modified allophanates are formed.

12. The process according to claim 9;
wherein a molar excess of component (b), based on component (a), is utilized in the reaction.

13. A process comprising:
reacting the reaction products according to claim 1 with at least one further reactive component to obtain copolymers.

14. The process according to claim 13;
wherein the at least one further reactive component is selected from the group consisting of alcohols, diols, polyols, thiols, amines, amino-functional polymers, aminoalkoxysilanes, alkoxysilanes, acrylated alcohols, organic alkoxylates, polyetherdiols, polyesterdiols, polytetrahydrofuran, silicone polyether copolymers, OH-functional polyether radicals, acid chlorides, and organofluorine compounds.

* * * * *